United States Patent [19]

Hugelin et al.

[11] 3,939,147

[45] Feb. 17, 1976

[54] NOVEL 1,2-DIAZA-1,5,9-CYCLO DODECATRIENES AND 1,2-DIAZA-1-CYCLODODECENES

[75] Inventors: Bernard Hugelin, Gaillard, France; Eduard Troxler, Basel, Switzerland

[73] Assignee: Ciba-Geigy Corporation, Ardsley, N.Y.

[22] Filed: June 14, 1973

[21] Appl. No.: 370,081

[30] Foreign Application Priority Data
June 16, 1972 Switzerland.......................... 9112/72

[52] U.S. Cl............ 260/239 BC; 71/92; 260/240 D; 260/240 K; 260/340.5; 260/566 B
[51] Int. Cl.$^2$.............. C07D 245/02; C07D 405/04; C07D 405/10; C07D 405/14
[58] Field of Search........ 260/239 BC, 240 D, 240 K

[56] References Cited
UNITED STATES PATENTS

| | | | |
|---|---|---|---|
| 3,238,265 | 3/1966 | Mueller et al. ...................... | 260/666 |
| 3,271,468 | 9/1966 | Wilke et al. ........................ | 260/668 |
| 3,641,175 | 2/1972 | Wilke et al...................... | 260/666 B |

FOREIGN PATENTS OR APPLICATIONS

| | | |
|---|---|---|
| 1,140,569 | 10/1966 | Germany |
| 56,783 | 7/1967 | Germany |
| 232,495 | 3/1964 | Austria |

OTHER PUBLICATIONS

Wilke, Pure and Applied Chemistry, Vol. 7, pp. 179-194 (1968).
Brenner et al., Liebig's Annalen des Chemie, Vol. 727, pp. 161-182 (1969).
Klein et al., Chemical Communications, 1971, pp. 42-43.
Bogdanovic et al., Liebigs Annalen des Chemie, Vol. 699, pp. 1-23 (1966).
Overberger et al., J. Am. Chem. Soc., Vol. 92, pp. 4922-4927 (1970).

*Primary Examiner*—Alton D. Rollins
*Attorney, Agent, or Firm*—Luther A. R. Hall

[57] ABSTRACT

New unsaturated 1,2-diazacyclododecanes, more particularly 1,2-diazacyclododecatrienes-1,5,9 and 1,2-diazacyclododecanes-1 and a novel process for the preparation thereof are disclosed which process comprises reacting a 1,3-diolefin with an azine in the presence of certain nickel catalysts. Said process unexpectedly yields 12-membered ring compounds only, and more especially oligomerization products of 2 mols of a 1,3-diolefin and 1 mol of an azine, while deactivation of the nickel catalyst by the -N=N-bond is avoided.

15 Claims, No Drawings

NOVEL 1,2-DIAZA-1,5,9-CYCLO DODECATRIENES AND 1,2-DIAZA-1-CYCLODODECENES

The present invention relates to new unsaturated 1,2-diazacyclododecanes and in particular 1,2-diazacyclododecatrienes-1,5,9 and 1,2-diazacyclododecanes-1, a new process for their manufacture and their use as biocidal active compounds, and the biocidal agents containing the new 1,2-diazacyclododecanes as active compounds.

It is known from the literature that the cyclotrimerisation of butadiene can be directed into a cyclodimerisation by the addition of suitable ligands (electron donors) to catalysts containing nickel.

It has been found that unsaturated 1,2-diazacyclododecanes of the formula Ia or Ib

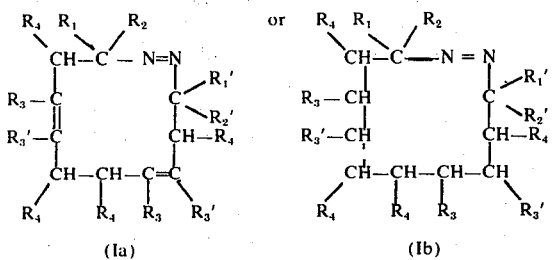

(Ia)                (Ib)

wherein $R_1$ and $R_1'$ independently of one another denote an aliphatic, cycloaliphatic, araliphatic or carbocyclic-aromatic hydrocarbon radical and $R_2$ and $R_2'$ independently of one another denote hydrogen or an aliphatic or cycloaliphatic hydrocarbon radical, or $R_1$ and $R_2$, or $R_1'$ and $R_2'$, together with the carbon atom to which they are bonded, form a cycloaliphatic ring, $R_4$ represents hydrogen or the methyl group and $R_3$ and $R_3'$ each represent hydrogen, or $R_3$ or $R_3'$ represents the methyl group if $R_4$ denotes hydrogen, are obtained in good to very good yields if a 1,3-diolefine of the formula II

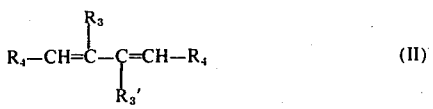

in which $R_3$, $R_3'$ and $R_4$ have the meaning given under formula I, is reacted at a temperature below 100°C with an azine of the formula III

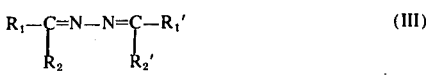

in which $R_1$, $R_1'$, $R_2$ and $R_2'$ have the meaning given under the formula I, in the presence of a catalyst which is obtained under reducing conditions by the action of an electron donor on compounds of nickel which are free of carbon monoxide, and the reaction product is optionally hydrogenated.

On the one hand, it is surprising that in spite of the use of nickel catalysts obtained by addition of electron donors no 8-membered rings but exclusively 12-membered rings are produced, and in particular that the co-oligomerisation products of 2 mols of 1,3-diolefine of the formula II and 1 mol of azine of the formula III are produced in high selectivity even if the 1,3-diolefine of the formula II is employed in excess. In contrast, in the known co-oligomerisation of 1,3-diolefines using analogous catalysts, for example in the cooligomerisation of 1,3-butadiene and isoprene, all other co-oligomerisation products are formed in approximately equal amounts alongside the predominantly produced cyclodimerisation product of 1,3-butadiene. On the other hand, surprisingly, no complex formation with the metal (nickel) takes place in the case of the systems according to the invention, whilst such is the case, for example, for azobenzenes; accordingly, the nickel catalyst is not deactivated by the —N=N— grouping and can be reused.

Aliphatic, cycloaliphatic, araliphatic or carbocyclicaromatic hydrocarbon radicals represented by $R_1$, $R_1'$, $R_2$ or $R_2'$ can be unsubstituted or substituted. Possible substituents are, for example, halogen atoms such as chlorine or bromine, trifluoromethyl, nitro, nitrile and phenyl groups, or alkyl, alkoxy, alkylamino, dialkylamino or alkylthio groups, each with 1 to 4 carbon atoms in the alkyl part.

Possible aliphatic hydrocarbon radicals having the meanings of $R_1$, $R_1'$, $R_2$ or $R_2'$ are above all optionally substituted alkyl or alkenyl radicals with up to 18, especially up to four carbon atoms. As examples of such radicals there may be mentioned: methyl, ethyl, isopropyl, n-propyl, 2-methylpropyl, 2,2-dimethylpropyl, n-butyl, 2-methylbutyl, 3-methylbutyl, 3,3-dimethylbutyl, but-2-enyl, n-pentyl, 4-methylpentyl, n-hexyl, n-octyl, n-decyl, n-dodecyl, n-pentadecyl, n-hexadecyl, n-heptadecyl, n-octadecyl and cinnamyl groups.

If $R_1$, $R_1'$, $R_2$ or $R_2'$ represent cycloaliphatic hydrocarbon radicals, they are, in particular, 3-members to 8-membered cycloalkyl radicals which are optionally substituted by methyl groups, especially methylcyclohexyl radicals and above all the cyclohexyl radical.

If $R_1$ or $R_1'$ denotes an araliphatic hydrocarbon radical, it is, for example, the phenethyl radical, but especially the benzyl radical.

Carbocyclic-aromatic hydrocarbon radicals which $R_1$ or $R_1'$ can represent can be mononuclear or polynuclear, substituted or unsubstituted and condensed with heterocyclic structures, above all 5-membered or 6-membered heterocyclic structures which contain O, S and/or N, for example with thiophene, furane, pyrrole, imidazole, pyrazole, pyridine, pyrimidine and pyridazine radicals. Examples of such carbocyclic-aromatic hydrocarbon radicals are the phenyl, 2-, 3- or 4-methylphenyl, 4-methoxyphenyl, 4-chlorophenyl, 3,5-dibromophenyl, 3-nitrophenyl, 3,5-dinitrophenyl, naphthyl-1, anthraquinone, fluorenone, benzofuran-6-yl, benzothien-6-yl, indol-6-yl and 3,4-methylenedioxyphenyl group. Preferably, $R_1$ or $R_1'$ represents a phenyl or naphthyl radical which is optionally substituted or condensed with a heterocyclic structure.

If $R_1$ and $R_2$, or $R_2'$ and $R_2'$, together with the carbon atom to which they are bonded, form a cycloaliphatic ring, the latter is preferably unsubstituted and has three to 12, especially five to 12, carbon atoms, such as the cyclopropyl, cyclopentyl, cyclohexyl, cyclooctyl and cyclododecyl ring.

In general, preferred unsaturated 1,2-diazacyclododecanes of the formula Ia or Ib according to the invention are those wherein $R_1$ and $R_1'$, or $R_2$ and $R_2'$, are identical and have the abovementioned preferred meaning.

According to a further preference, $R_1$ and $R_1'$ each represent a alkyl or alkenyl radical with up to four carbon atoms which is optionally substituted by a phenyl group, the cyclohexyl radical, a phenyl radical which is optionally substituted in the 4-position by a halogen atom or an alkyl or alkoxy group with 1 to 4 carbon atoms, especially a chlorine atom or a methoxy group, the naphthyl-1 radical or the 3,4-methylenedioxyphenyl radical, and $R_2$, $R_2'$, $R_3'$ and $R_4$ each represent hydrogen.

Further preferred unsaturated 1,2-diazacyclododecanes of the formula Ia or Ib are those wherein $R_1$, $R_1'$, $R_2$ and $R_2'$ each represent a saturated, unsubstituted alkyl radical with one to four carbon atoms, especially the methyl group, or $R_1$ and $R_2$, as well as $R_1'$ and $R_2'$, each form, together with the carbon atom to which they are bonded, an unsubstituted cycloaliphatic ring with five to 12 carbon atoms, and $R_3$, $R_3'$ and $R_4$ each denote hydrogen.

1,2-Diazacyclododecatriene-1,5,9 of the formula I, wherein $R_1$ and $R_1'$ each denote the ethyl group and $R_2$, $R_2'$, $R_3$, $R_3'$ and $R_4$ each denote hydrogen, has proved particularly valuable.

The 1,3-diolefines of the formula II used as starting products, namely butadiene-1,3,2-methyl-butadiene-1,3 and hexadiene-2,4, are known. Butadiene-1,3 is preferentially used in the process according to the invention.

The azines of the formula III are also known or can be manufactured in a manner which is in itself known. Symmetrical azines, that is to say compounds of the formula III in which $R_1$ and $R_1'$ or $R_2$ and $R_2'$ are each identical can be manufactured, for example, by condensation of appropriate aldehydes or ketones with hydrazine or hydrazine derivatives, such as hydrazine hydrate, hydrazine sulphate or hydrazine hydrochloride.

Asymmetrical azines, that is to say compounds of the formula III in which $R_1$ and $R_1'$, and/or $R_2$ and $R_2'$, have different meanings can be obtained, for example, by reaction of a hydrazone with aldehydes, ketones or quinones or by reaction of a hydrazone with the Schiff's base of an aldehyde.

The following may be mentioned as examples of suitable azines of the formula III: diethylidenehydrazine (acetaldazine), di-n-propylidenehydrazine (propionaldazine), di-n-butylidenehydrazine n-butyraldazine), bis-(2-methylpropylidene)-hydrazine (isobutyraldazine), bis-(2,2-dimethylpropylidene)-hydrazine (neopentanaldazine), bis-(3,3-dimethylbutylidene)-hydrazine, bis-(2-methylbutylidene)-hydrazine (isopentanaldazine), di-n-pentylidenehydrazine, di-n-hexylidenehydrazine, di-n-heptylidenehydrazine, di-n-octylidenehydrazine, di-n-nonylidenehydrazine, di-n-decylidenehydrazine, di-n-dodecylidenehydrazine, di-n-pentadecylidenehydrazine, di-h-hexadecylidenehydrazine, di-n-heptadecylidenehydrazine, di-n-octadecylidenehydrazine, dibuten-2-ylidenehydrazine (crotonaldazine), dicinnamylidenehydrazine, bis-(cyclopropyl-methylidene)-hydrazine, bis-(cyclobutyl-methylidene)-hydrazine, bis-(cyclohexyl-methylidene)-hydrazine, bis-(cyclooctyl-methylidene)-hydrazine, bis-(phenethylidene)-hydrazine, bis-(γ-phenylpropylidene)-hydrazine, dibenzylidenehydrazine (benzaldazine), bis-(4-chlorobenzylidene)-hydrazine, bis-(3-nitrobenzylidene)-hydrazine, bis-(2-, 3- or 4-methylbenzylidene)-hydrazine, bis-(4-methoxybenzylidene)-hydrazine (p-anisaldazine),bis-(naphth-1-yl-methylidene)-hydrazine (naphthalene-1-aldazine), bis-(3,4- methylenedioxybenzylidene)-hydrazine (piperonaldazine), di-isopropylidenehydrazine (acetonazine), bis-[butylidene-(2)]-hydrazine (butanonazine), bis-[3-methyl-butyliden-(2)]-hydrazine, bis-[3,3-dimethyl-butylidene-(2)]-hydrazine, bis-[pentylidene-(2)]-hydrazine, bis-[pentylidene-(3)]-hydrazine, bis-[4-methyl-pentylidene-(2)]-hydrazine, bis-[hexylidene-(2)]-hydrazine, bis-[heptylidene-(3)]-hydrazine, bis-(dicyclohexyl-methylidene)-hydrazine, ethylidene-3-nitrobenzylidene)-hydrazine, (3-nitrobenzylidene)-benzylidene-hydrazine, dicyclohexylidenehydrazine (cyclohexanonazine), and dicyclododecylidenehydrazine (cyclododecanonazine).

The catalysts which can be used in the process according to the invention are in themselves known; preferably, catalysts are used which are obtained by the reduction of compounds of nickel which are free of carbon monoxide, with organo-metallic compounds which are free of halogen, such as metal-alkyls or metal-aryls, in the presence of electron donors.

Examples of suitable compounds of nickel which are free of carbon monoxide are nickel acetylacetonate, nickel dimethylglyoxime, nickel formate and dicyclopentadienyl-nickel; nickel acetylacetonate is preferred.

Possible metal-alkyls or metal-aryls according to the definition are, for example, n-butyl-lithium or methyl-lithium, trimethyl-aluminium or triethyl-aluminium, ethoxydiethyl-aluminium, tributyl-gallium and diethyl-zinc; the use of ethoxy-diethyl-aluminium as a reducing agent has proved particularly advantageous.

The electron donors used are Lewis bases, such as cyclic ethers, alkylphosphines or arylphosphines, alkylphosphites or arylphosphites and the corresponding compounds of arsenic and antimony, for example dioxane, tetrahydrofurane, tetrahydropyrane, triethylphosphine, tricyclohexylphosphine, triphenylphosphine, triethylarsine, triethylarsine, triphenylarsine, triphenylantimony, triphenylphosphite, tris-o-cresyl-phosphite, tris-o-methoxyphenyl-phosphite, o-biphenylyl-diphenylphosphite and tris-o-biphenylyl-phosphite. Triphenylphosphine is used preferentially.

The nickel compound and the electron donor are appropriately used in a mutual molar ratio of 1:1 to about 1:3, whilst the reducing agent is used in an approximately 2-fold to 10-fold excess, relative to the nickel compound.

Usually, the catalyst is manufactured in situ by reduction of the nickel compound which is free of carbon monoxide, in the presence of the electron donor, in an inert solvent which already contains the starting diolefine of the formula II. The reduction can be carried out through addition of one of the abovementioned reducing agents or electrolytically. On the other hand, it is also possible to use, for the reaction of the 1,3-diolefine of the formula II with the azine of the formula III, a nickel-O-complex which has been isolated beforehand, such as the ethylene-bis-(triphenylphosphine)-Ni-(O)-complex, the bis-cyclooctadiene-(1,5)-nickel(O)-complex or the trans-cyclododecatriene-(1,5,9)-nickel(O)-complex.

The reaction according to the invention is advantageously carried out in the presence of an inert organic solvent. Possible solvents are, in particular, optionally halogenated aliphatic or aromatic hydrocarbons or aliphatic and cycloaliphatic ethers, such as n-hexane, n-heptane, benzene, toluene, chlorobenzene, diethyl ether and dioxane. It is very particularly preferred to carry out the reaction under anhydrous conditions, above all in anhydrous toluene. It is however also possible to use an excess of the starting diolefine of the formula II as the solvent both already during the manufacture of the catalyst and during the subsequent reaction with the azine of the formula III.

If the reaction is carried out in the presence of an organic solvent it is possible — without significantly impairing the yields of 1,2-diazacyclododecatrienes-1,5,9 of the formula Ia — to work either with stoichiometric amounts of 1,3-diolefine of the formula II and azine of the formula III or with a slight excess of 1,3-diolefine.

The process according to the invention can be carried out under normal pressure or under excess pressure, for example under an excess pressure of up to about 10 bars; preferably, an initial pressure of about 1 bar is used.

Though the reaction can be carried out at temperatures of up to 100°C, a temperature range of 20°C to 40°C is preferred. Furthermore, it is advisable to carry out the reaction under a protective gas, such as nitrogen or argon.

The 1,2-diazacyclododecatrienes-1,5,9 of the formula Ia obtained after the reaction can, if desired, be converted into the corresponding 1,2-diazacyclododecenes-1 of the formula Ib in a manner which is in itself known, by hydrogenation, for example by catalytic hydrogenation.

The 1,2-diazacyclododecatrienes-1,5,9 of the formula Ia, manufactured according to the invention, can be isolated and purified in the usual manner, for example by means of repeated distillation.

The new unsaturated 1,2-diazacyclododecanes of the formula Ia or Ib are colourless to slightly yellowish liquids or crystals and can be in either the trans-configuration or the cis-configuration but are predominantly obtained in the trans-form. In the formulae of the examples which follow, all compounds have therefore been represented in the transform. The reactions were carried out under a protective gas (nitrogen or argon).

EXAMPLE 1

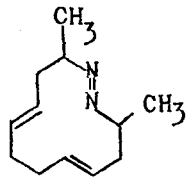

2.2 g (8.5 mmols) of nickel acetylacetonate and 2.2 g (8.4 mmols) of triphenylphosphine in 100 ml of absolute toluene, in which 40 g (0.74 mol) of butadiene-1,3 are dissolved, are reduced with 3.2 ml (21 mmols) of ethoxy-diethyl-aluminium at 0°C to 20°C. After stirring the reaction mixture for 1 hour at 20°C, a clear, orange-red-coloured catalyst solution results. Thereafter 20 g (0.24 mol) of diethylidene-hydrazine (acetaldazine) are added in one portion to the catalyst solution at 0°C and after a further hour the reaction mixture is warmed to 30°C and kept for 20 hours at this temperature (initial pressure approx. 1 bar). Thereafter the reaction is interrupted and the reaction solution is subjected to a distillation at $10^{-3}$ mm Hg and a bath temperature of maximally 100°C. After a further fine distillation using a split-tube column, 31.5 g of 3,12-dimethyl-1,2-diazacyclododecatriene-1,5,9 are obtained; yield: 69% of theory, relative to diethylidenehydrazine reacted (conversion 100%); boiling point (0.2 mm Hg) = 63°–66°C; $n_D^{20}$ = 1.4861. The residue contained 6 g of higher polymers in addition to the catalyst.

MS-spectrum: molecule peak 192, fragment masses 177, 82, 67 and 54;

$H^1$—NMR spectrum: $\delta$ = 5(m), 3.5–3.8(m), 1.5–2.8(m), 1.2(d) in the ratio of 4:2:8:6.

EXAMPLE 2

2.2 g (8.5 mmols) of nickel acetylacetonate and 2.2 g (8.4 mmols) of triphenylphosphine, in 100 ml of anhydrous benzene in which 41 g (0.75 mol) of butadiene-1,3 are dissolved, are reduced with 2.7 ml (20 mmols) of triethyl-aluminium at 0°– 20°C. After carrying out the catalysis and working up the reaction product as indicated in Example 1, the same amount of 3,12-dimethyl-1,2-diazacyclododecatriene-1,5,9 is obtained.

EXAMPLE 3

If the procedure indicated in Example 1 is followed but instead of 2.2 g (8.4 mmols) of triphenylphosphine 2.6 g (8.4 mmols) of triphenylphosphite are used, 3,12-dimethyl-1,2-diazacyclododecatriene-1,5,9 is obtained in practically the same yield as in Example 1, after a reaction time of 15 days and working up the reaction product as in the example mentioned.

EXAMPLE 4

If the procedure indicated in Example 1 is followed but instead of 2.2 g (8.4 mmols) of triphenylphosphine 3.09 g (8.4 mmols) of tris-o-cresyl-phosphite are used, 3,12-dimethyl-1,2-diazacyclododecatriene-1,5,9 is obtained in practically the same yield as in Example 1, after a reaction time of 22 days and working up the reaction product as indicated in the example mentioned.

EXAMPLE 5

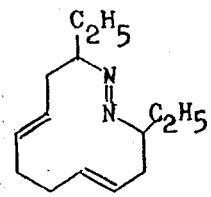

If, whilst otherwise following the same procedure, the diethylidenehydrazine in Example 1 is replaced by 20 g (0.178 mol) of di-n-propylidenehydrazine (propionaldazine), 34.8 g of 3,12-diethyl-1,2-diazacyclododecatriene-1,5,9 are obtained after working up and fine distillation of the reaction product at $10^{-3}$ mm Hg as described in Example 1; yield: 89% of theory relative to di-n-propylidenehydrazine converted (conversion 100%); boiling point (0.01 mm Hg) = 63°C.

MS-spectrum: molecule peak 220, fragment masses 191, 96, 81, 67 and 54.

$H^1$-NMR spectrum: $\delta$ = 5(m), 3.7 (m), 3.3 (m), 2.9–1.5 (m), 0.8 (t) in the ratio of 4 : 2 : 12 : 6.

EXAMPLE 6

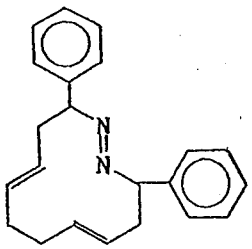

A catalyst solution is prepared as described in Example 1 and 20 g (0.096 mol) of dibenzylidenehydrazine (benzaldazine) are added thereto. After 48 hours, the reaction is interrupted, and the mixture is distilled, directly from the reaction vessel, at $10^{-2}$ mm Hg and a bath temperature of at most 90°C. Sufficient boiling ethanol is added to the distillation residue that the entire residue dissolves. After recrystallisation from ethanol, 18 g of 3,12-diphenyl-1,2-diazacyclododecatriene-1,5,9 are obtained as colourless crystals; yield 58% of theory, relative to dibenzylidenehydrazine converted (conversion 100%); melting point 146°–147°C. MS-spectrum: molecule peak 316, fragment masses 288, 144, 143, 129, 91, 77 and 66.

$H^1$—NMR spectrum: $\delta$ = 7.3(s), 5.15(m), 4.28–4.60 (each 2d), 3.5–1.7 (m) in the ratio of 10:4:2:8.

Analysis for $C_{22}H_{24}N_2$: Calculated—C 83.48%, H 7.65%, N 8.86%. Found—C 83.49%, H 7.66%, N 9.03%.

EXAMPLE 7

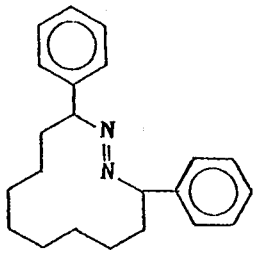

3,12-Diphenyl-1,2-diazacyclododecatriene-1,5,9, manufactured according to Example 6, is hydrogenated under normal pressure and at room temperature (approx. 25°C) on a platinum-charcoal catalyst (5% platinum); 2 mols of hydrogen are taken up and 3,12-diphenyl-1,2-diazacyclododecene-1 is obtained; melting point 79-80°C. The 1,2-diazacyclododecatrienes-1,5,9, described in the remaining examples can be hydrogenated analogously.

EXAMPLE 8

If in Example 6, whilst otherwise following the same procedure, only the stoichiometrically required amount (11 g = 0.2 mol) of butadiene-1,3 is used instead of an excess, 3,12-diphenyl-1,2-diazacyclododecatriene-1,5,9 is obtained in practically the same yield.

EXAMPLE 9

2.75 g (10 mmols) of bis-cyclooctadiene-1,5-nickel-(O) and 2.62 g (10 mmols) of triphenylphosphine are dissolved in 300 ml of anhydrous benzene which contains 54 g (1 mol) of butadiene-1,3, at −10°C to 0°C. A clear, homogeneous orange-coloured solution results. Thereafter, 52.8 g (0.25 mol) of dibenzylidenehydrazine (benzaldazine) are added and the reaction mixture is stirred for 48 hours at 20°C. After working up the reaction product as indicated in Example 6, 3,12-diphenyl-1,2-diazacyclododecatriene-1,5,9 is obtained in practically the same yield as in Example 6.

EXAMPLE 10

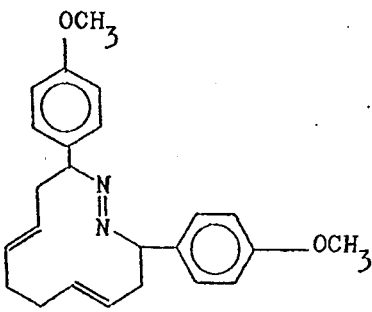

A catalyst solution is prepared as described in Example 1 and 20 g (0.075 mol) of bis-(4-methoxybenzylidene)-hydrazine (p-anisaldazine) are subsequently added thereto. After a reaction time of 15 hours at 30°C, the reaction mixture is cooled to −70°C and filtered, and the filter residue is washed with cold diethyl ether. 20.1 g of 3,12-di-4-methoxyphenyl-1,2-diazacyclododecatriene-1,5,9 are thus obtained in the form of colourless crystals; melting point 167°–169°C. A further 2.1 g of the product of the above formula can be obtained by concentrating the mother liquor; yield 79% of theory, relative to bis-(4-methoxy-benzylidene)-hydrazine converted (conversion 100%).

MS spectrum: molecule peak 376, fragment masses 348, 240, 173, 159, 121 and 91.

$H^1$-NMR spectrum: $\delta$ = 6.85–7.45(m), 5.25(m), 4.28–4.64 (each 2d), 3.80 (s), 1.80–3.30 (m) in the ratio of 8:4:2:6:8.

Analysis for $C_{24}H_{28}N_2O_2$: Calculated—C 76.56%, H 7.50%, N 7.44%. Found—C 76.70%, H 7.60%, N 7.50%.

EXAMPLE 11

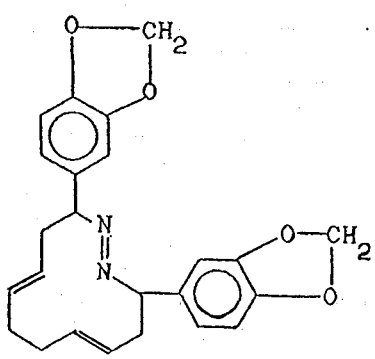

If, whilst otherwise following the same procedure, the dibenzylidenehydrazine in Example 6 is replaced by 20 g (0.067 mol) of piperonaldazine, 19.2 g of 3,12-di-(3,4-methylenedioxyphenyl)-1,2-diazacyclododeca-triene-1,5,9 are obtained; melting point 160°–161°C (decomposition); yield 71% of theory, relative to piperonaldazine converted (conversion 100%).

MS spectrum: molecule peak 404, fragment masses 376, 268, 188, 187, 173, 157 and 135.

H$^1$—NMR spectrum: δ = 6.98 (s), 6.85 (s), 6.0 (s), 5.25 (m), 4.20–4.58 (2d), 1.7–3.3 (m) in the ratio of 2:4:4:4:2:8.

Analysis for $C_{24}H_{24}N_2O_4$: Calculated—C 71.25%, H 5.98%, N 6.93%. Found—C 70.80%, H 6.10%, N 6.90%.

EXAMPLE 12

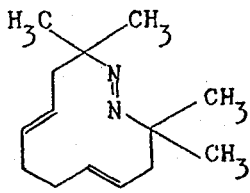

If, whilst otherwise using the same procedure, twice the amount of catalyst (nickel acetylacetonate and triphenylphosphine) is used in Example 1, and instead of 20 g of diethylidenehydrazine 55.4 g (0.494 mol) of diisopropylidenehydrazine (acetonazine) are used, 69 g of 3,3',12,12'-tetramethyl-1,2-diazacyclododeca-triene-1,5,9 are obtained, in the form of a colourless liquid, after distillation using a split tube column; boiling point (0.03 mm Hg) = 63°C; yield 64% of theory relative to diisopropylidenehydrazine converted (conversion 100%).

MS spectrum: molecule peak 220, fragment masses 205, 192. 96 and 81.

H$^1$—NMR spectrum: δ = 4.95 (m), 2.35–2.50 (m), 1.90–2.10 (m), 1.15 (s) in the ratio of 4:4:4:12.

EXAMPLE 13

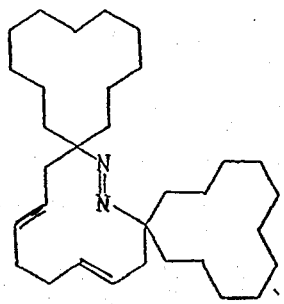

The procedure described in Example 6 is followed but using 14.4 g (0.04 mol) of dicyclododecylidenehydrazine (cyclododecanonazine) instead of 20 g of dibenzylidene-hydrazine, and carrying out the reaction at 35°C for 40 hours. From the distillation residue, 3.0 g of the compound of the above formula can be isolated, in the manner described in Example 6, in the form of colourless crystals; melting point 195°–196°C; yield 32% of theory relative to dicyclododecylidenehydrazine converted (conversion 50%).

MS spectrum: molecule peak 468, fragment masses 440, 220 and 166.

H$^1$—NMR spectrum: δ = 5 (m), 2.35–2.55 (m), 1.90–2.10 (m), 1.55 (s), 1.40 (s) in the ratio of 4:4:4:8:36.

Analysis for $C_{32}H_{56}N_2$: Calculated—C 81.9%, H 12.06%, N 5.99%, Found—81.3%, H 12.1%, N 6.2%.

EXAMPLE 14

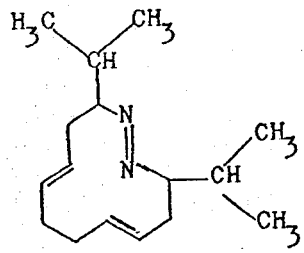

If, whilst otherwise following the same procedure, the 20 g of diethylidenehydrazine in Example 1 are replaced by 16.6 g (0.12 mol) of bis-(2-methyl-propylidene)-hydrazine (isobutyraldazine), 21.3 g of 3.12-diisopropyl-1,2-diazacyclododecatriene-1,5,9 are obtained after the fine distillation at 1 mm Hg; boiling point (1 mm Hg) = 124°C; yield 72% of theory relative to bis-(2-methylpropylidene)-hydrazine converted (conversion 100%).

MS spectrum: molecule peak 248, fragment masses 205, 110 and 95.

H$^1$-NMR spectrum: δ = 5.1 (m), 3.75 (m), 3.05 (m), 1.5–2.9 (m), 0.85–1.15 (each 2d) in the ratio of 4:2:2:8:12.

EXAMPLE 15

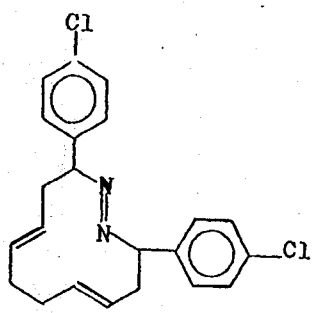

Example 10 is repeated but using, instead of 20 g of bis-(4-methoxybenzylidene)-hydrazine, 20 g (0.072 mol) of bis-(4-chlorobenzylidene)-hydrazine (p-chlorobenzaldazine). After working up the reaction product as described and recrystallising it once from toluene, 4.15 g of 3,12-di-4-chlorophenyl-1,2-diazacyclododecatriene-1,5,9 are obtained in the form of colourless crystals; melting point 155°–158°C (decomposition); yield 15% of theory relative to bis-(4-chlorobenzylidene)-hydrazine converted (conversion 100%).

MS spectrum: molecule peak 384, 386 and 388, (6:4:1), fragment masses 356, 358, 360 (6:4:1), 178, 180 (3:1), 177, 179, (3:1), 163, 165 (3:1) and 143.

H$^1$-NMR spectrum: δ — 7.4 (m), 5.25 (m), 4.28–4.62 (each 2d), 1.9–3.4 (m) in the ratio of 8:4:2:8.

Analysis for $C_{22}H_{22}N_2Cl_2$: Calculated—C 68.64%, H 5.76%, N 7.28%. Found—C 68.97%, H 5.86%, N 7.06%.

EXAMPLE 16

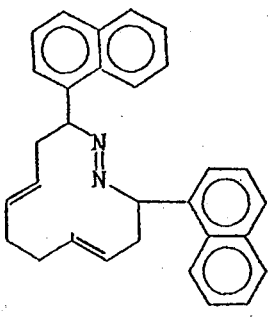

2.2 g (8.5 mmols) of nickel acetylacetonate and 2.2 g (8.4 mmols) of triphenylphosphine, in 100 ml of anhydrous toluene in which 13.86 g (0.256 mol) of butadiene-1,3 are dissolved, are reduced with 3.2 ml (21 mmols) of ethoxy-diethyl-aluminium at 0°C to 20°C. After stirring the reaction mixture for 1 hour at 20°C, a clear, orange-red-coloured solution is produced. To this solution, 15 g (0.0485 mol) of naphthalene-1-aldazine are subsequently added in one portion, at 0°C. Thereafter the reaction mixture is warmed to 30°C and kept at this temperature for 18 hours. After this time, the reaction is interrupted and the mixture is distilled directly from the reaction vessel, at 10$^{-3}$ mm Hg and a bath temperature of —70°C to +10°C, into a receiver cooled with liquid nitrogen. The residue is washed with cold diethyl ether. 10 g of slightly yellowish-coloured crystals of 3,12-dinaphthyl-1,2-diazacyclododecatriene-1,5,9 are left; after recrystallisation from ethanol, these are colourless and have a melting point of 129°C (decomposition); yield 49% of theory, relative to naphthalene-1-aldazine converted (conversion 100%).

MS spectrum: molecule peak 416, fragment masses 388, 277, 194, 193 and 179.

H$^1$—NMR spectrum: δ = 7.12–8.22 (m), 5.92–6.34 (2d), 5.37 (m), 2.95 (m), 2.18 (m) in the ratio of 14:2:4:4:4.

Analysis for $C_{30}H_{28}N_2$: Calculated — C 86.5%, H 6.78%, N 6.73%. Found — C 85.8%, H 6.8%, N 6.6%.

EXAMPLE 17

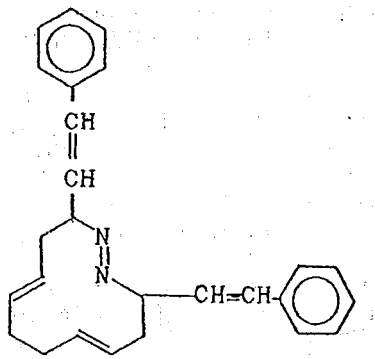

Example 16 is repeated but using 10 g (0.185 mol) of butadiene-1,3 instead of 13.86 g and 15 g (0.0575 mol) of dicinnamylidenehydrazine (cinnamaldazine) instead of 15 g of naphthalene-1-aldazine. 12.6 g of 3,12-distyryl-1,2-diazacyclododecatriene-1,5,9 are obtained in the form of slightly yellowish-coloured crystals; melting point 135°C; yield 58% of theory relative to cinnamaldazine converted (conversion 100%).

MS spectrum: molecule peak 368, fragment masses 340, 170, 169 and 155.

H$^1$-NMR spectrum: δ = 7.30 (m), 6.5 (d), 5.2 (m), 3.88–4.35 (each 2d), 1.70–3.30 (m) in the ratio of 10:4:4:2:8.

Analysis for $C_{26}H_{28}N_2$: Calculated — C 84.7%, H 7.9%, N 7.6%. Found — C 84.65%, H 7.77%, N 7.37%.

EXAMPLE 18

Example 6 is repeated, but using 13.6 g (0.255 mol) of butadiene-1,3 instead of 40 g, and 20 g (0.104 mol) of dicyclohexylidenehydrazine (cyclohexanonazine) instead of 20 g of dibenzylidenehydrazine. 16.3 g of 1,2-diazacyclododecatriene-1,5,9 of the formula

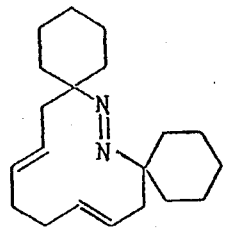

are obtained in the form of colourless crystals; melting point 62–64°C; yield 52% of theory relative to cyclohexanonazine converted (conversion 100%).

MS spectrum: molecule peak 300, fragment masses 272, 136, 135 and 121.

H$^1$—NMR spectrum: δ = 4.98 (m), 2.45 (m), 1.98 (m), 1.4–1.80 (m) in the ratio of 4:4:4:20.

Analysis for $C_{20}H_{32}N_2$: Calculated — C 80.07%, H 10.75%, N 9.3%. Found — C 79.0%, H 10.7%, N 8.9%.

EXAMPLE 19

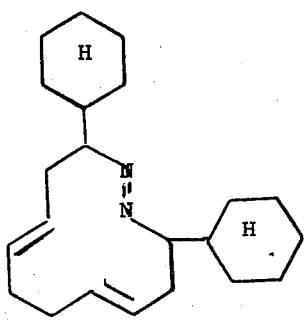

2.2 g (8.5 mmols) of nickel acetylacetonate and 2.2 g (8.4 mmols) of triphenylphosphine, in 100 ml of anhydrous toluene in which 52 g (0.965 mol) of butadiene-1,3 are dissolved, are reduced with 3.2 ml (21 mmols) of ethoxy-diethyl-aluminium at 0°C to 20°C. After stirring the reaction mixture for 1 hour at 20°C, a clear solution, coloured orange-red, is obtained. Thereafter, 54 g (0.24 mol) of bis-(cyclohexyl-methylidene)-hydrazine (cyclohexylaldazine) are added to this solution in one portion, at 0°C, and the reaction mixture is stirred further at room temperature. After 40 minutes, a strongly exothermic reaction occurs. The reaction mixture is cooled to −70°C, the product which has precipitated is filtered off, and the filter residue is washed with cold diethyl ether and dried.

58 g of 3,12-dicyclohexyl-1,2-diazacyclododeca-triene-1,5,9 are obtained as colourless crystals of melting point 102°–103°C; yield 79% of theory relative to bis-(cyclohexyl-methylidene)-hydrazine converted (conversion 100%). A further 4.4 g of 3,12-dicyclohexyl-1,2-diazacyclododecatriene-1,5,9 can be isolated by concentrating the mother liquor, corresponding to a total yield of 85% of theory. MS spectrum: molecule peak 328, fragment masses 300, 245, 150, 149 and 135.

$H^1$—NMR spectrum: $\delta = 4.95$ (m), $3.10$ (m), $2.50$ (m), $1.40$–$2.35$ (m), $1.15$ (d) in the ratio of 4:2:4:18:8.

Analysis for $C_{22}H_{36}N_2$: Calculated — C 80.42%, H 11.04%, N 8.53%. Found — C 80.44%, H 10.96%, N 8.53%.

EXAMPLE 20

If the procedure indicated in Example 19 is followed but using a reaction temperature of 40°C and passing in butadiene-1,3 so that all the butadiene-1,3 is absorbed immediately (pressure-free process), the same reaction time and working up of the reaction product as in the example mentioned gives 3,12-dicyclohexyl-1,2-diazacyclododecatriene-1,5,9 in practically the same yield.

EXAMPLE 21

Example 6 is repeated, but using 16.5 g of dicyclopentylidenehydrazine (cyclopentanonazine) instead of 20 g of dibenzylidenehydrazine. 18 g of 1,2-diazacyclododecatriene-1,5,9 of the formula

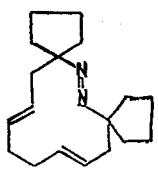

are isolated; yield 66% of theory relative to cyclopentanonazine converted (conversion 100%).

MS spectrum: molecule peak 272, 244, 122 and 107.

$H^1$—NMR spectrum: $\delta = 5.0$ (m), $2.46$ (m), $1.98$ (m), $1.5$–$1.80$ (m) in the ratio of 4:4:4:16.

EXAMPLE 22

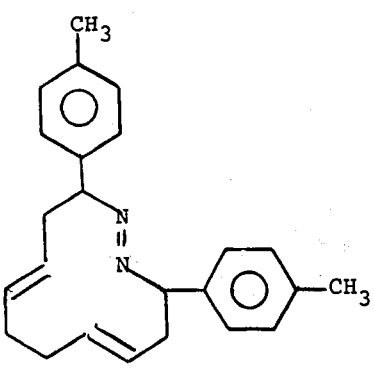

If in Example 6, whilst otherwise following the same procedure, 20 g (0.096 mol) of dibenzylidenehydrazine (benzaldazine) are replaced by 24 g (0.1 mol) of bis-(4-methyl-benzylidene)-hydrazine, the same working up and recrystallisation from ethanol gives 27 g of 3,12-di-4-methylphenyl-1,2-diazacyclododecatriene-1,5,9 in the form of colourless crystals; melting point 155°C; yield 78% of theory relative to bis-(4-methyl-benzylidene)-hydrazine converted (conversion 100%).

MS spectrum: molecule peak 344, fragment masses 316, 158, 157 and 143.

$H^1$—NMR spectrum: $\delta = 7.3$ (m), $5.26$ (m), $4.28$–$4.61$ (each 2d), $3.2$–$1.8$ (m) in the ratio of 8:4:2:14.

EXAMPLE 23

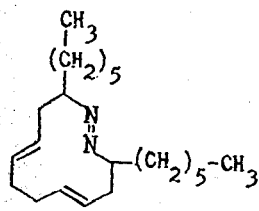

If in Example 1, whilst otherwise following the same procedure, the diethylidenehydrazine is replaced by 54 g (0.24 mol) of di-n-hepthylidenehydrazine, working up and molecular distillation at 0.01 mm Hg and 140°C bath temperature gives 3,12-di-n-hexyl-1,2-diazacyclododecatriene-1,5,9 as a viscous oil; yield 56 g = 68% of theory, relative to di-n-heptylidenehydrazine converted (conversion 100%).

MS spectrum: molecule peak 332, fragment masses 304, 247, 152, 151 and 137.

$H^1$—NMR spectrum: $\delta = 5$ (m), $3.3$–$3.9$ (m), $2.9$–$15$ (m), $0.8$ (t) in the ratio of 4:2:28:6.

The new 1,2-diazacyclododecanes of the formula I$a$ or I$b$ possess biocidal, especially herbicidal, properties and are suitable for combating pests of all kinds, for example for use as pre-emergence herbicides for combating grass-like weeds in various crop plantings.

The activity of the new compounds was determined from the following experiment:

Herbicidal action on application before emergence of the plant (pre-emergence use)

Immediately after sowing the test plants, the surface of the ground is treated with an aqueous suspension of the active substance obtained from a 25% strength wettable powder. The amount used is chosen to correspond to 16 kg of active substance per hectare. The seed dishes are kept in a greenhouse at 22°–25°C and 50–70% relative atmospheric humidity.

The test plants used are:
*Avena sativa*
*Setaria italica*
*Lolium perenne*.

20 days after application of the active substance, the test is evaluated. In this test, the 3,12-diethyl-1,2- diazacyclododecatriene-1,5,9 manufactured according to Example 5 showed an excellent herbicidal action.

Biocidal agents according to the invention are manufactured in a manner which is in itself known by intimate mixing and grinding of active substances of the formula Ia or Ib with suitable carriers, optionally with addition of dispersing agents or solvents which are inert towards the active substances. The active substances can exist, and be used, in the following forms of preparations:

Solid forms of preparations: dusting agents, sprinkling agents, granules, encapsulated granules, impregnated granules and homogeneous granules.

Active substance concentrates which can be dispersed in water: wettable powders, pastes and emulsions.

Liquid forms of preparations: solutions and aerosols.

To manufacture solid forms of preparations (dusting agents, sprinkling agents and granules), the active substances are mixed with solid carriers. Possible carriers are, for example, kaolin, talc, bolus, loess, chalk, limestone, lime grits, attaclay, dolomite, diatomaceous earth, precipitated silica, alkaline earth metal silicates, sodium aluminium silicates and potassium aluminium silicates (feldspars and micas), calcium sulphate and magnesium sulphate, magnesium oxide, ground plastics, fertilisers, such as ammonium sulphate, ammonium phosphate, ammonium nitrate and urea, ground vegetable products, such as cereal flour, powdered bark, wood flour, nutshell powder, cellulose powder, residues from plant extractions, active charcoal and the like, individually or as mixtures with one another.

The particle size of the carriers is appropriately up to approx. 0.1 mm for dusting agents, approx. 0.075 to 0.2 mm for sprinkling agents and 0.2 mm or above for granules. The active substance concentrations in the solid forms of preparations are as a rule 0.5 to 80%. It is furthermore possible to add, to these mixtures, additives which stabilise the active substance and/or nonionic, anionic and cationic substances which, for example, improve the adhesion of the active substances to plants and parts of plants (adhesives and glues) and/or ensure better wettability (wetting agents) as well as dispersibility (dispersing agents).

Possible adhesives are, for example, the following: olein-lime mixtures, cellulose derivatives (methylcellulose or carboxymethylcellulose), hydroxyethylene glycol ethers of monoalkylphenols and dialkylphenols with 5 – 15 ethylene oxide residues per molecule and 8 – 9 carbon atoms in the alkyl radical, ligninsulphonic acid, its alkali metal salts and alkaline earth metal salts, polyethylene glycols (Carbowaxes), fatty alcohol polyethylene glycol ethers with 5 – 20 ethylene oxide radicals per molecule and 8 – 18 carbon atoms in the fatty alcohol part, condensation products of ethylene oxide or propylene oxide, polyvinylpyrrolidones, polyvinyl alcohols, condensation products of urea-formaldehyde, and latex products.

Water-dispersible active substance concentrates, that is to say wettable powders, pastes and emulsion concentrates, are agents which can be diluted with water to any desired concentration. They consist generally of active substance, carrier, surface-active substances and anti-foaming agents and optionally solvents. The active substance concentration in these agents is about 5 – 80%. The wettable powders and pastes are obtained by mixing and grinding the active substances with dispersing agents and pulverulent carriers in suitable apparatuses until the mixture is homogeneous. In some cases it is advantageous to use mixtures of different carriers.

Examples of dispersing agents which can be used are: condensation products of sulphonated naphthalene and sulphonated naphthalene derivatives with formaldehyde, condensation products of naphthalene or of naphthalenesulphonic acids with phenol and formaldehyde and alkali metal salts, ammonium salts and alkaline earth metal salts of ligninsulphonic acid, as well as alkylarylsulphonates, alkali metal salts and alkaline earth metal salts of dibutylnaphthalenesulphonic acid, fatty alcohol sulphates, such as salts of sulphated hexadecanols, heptadecanols and octadecanols and salts of sulphated fatty alcohol polyethylene glycol ethers, the sodium salt of oleyl-methyl-tauride, dialkyldilaurylammonium chloride and fatty acid salts of alkali metals and alkaline earth metals.

Silicones, for example, can be used as anti-foaming agents.

The active substances are mixed with the abovementioned additives, ground, sieved and graded so that in the case of wettable powders the solid constituent does not exceed a particle size of 0.02 to 0.04 mm and in the case of pastes it does not exceed 0.03 mm. Dispersing agents, such as are listed in the preceding sections, organic solvents and water are used for the manufacture of emulsion concentrates and pastes.

Examples of solvents are, for example, alcohols, benzene, xylenes, toluene, dimethylsulphoxide and mineral oil fractions which boil in the range of 120°C to 350°C. The solvents must be practically odourless, non-phytotoxic and inert towards the active substances and must not be easily inflammable.

The agents according to the invention can furthermore be used in the form of solutions. For this, the active substance, or several active substances, of the formula Ia or Ib are dissolved in suitable organic solvents, solvent mixtures, water or mixtures of organic solvents with water. Aliphatic and aromatic hydrocarbons, their chlorinated derivatives, alkylnaphthalenes and mineral oils, by themselves or as a mixture with one another, can be used as organic solvents. The solutions should contain the active substances in a concentration range of 1 to 20%.

These solutions can be applied either with the aid of a propellant gas (as a spray) or by means of special spray guns (as an aerosol).

Other biocidal active substances or agents can be mixed into the agents according to the invention, which have been described to broaden the spectrum of action. Thus the new agents can for example contain, in addition to the compounds of the formula Ia or Ib, insecticides, fungicides, bactericides, fungistatic agents, bacteriostatic agents or nematocides, for broadening the spectrum of action. The agents according to the invention can furthermore also contain plant fertilisers, trace elements and the like.

Some forms of preparations of the new active substances are described below by way of examples. Unless stated to the contrary, parts denote parts by weight.

Dusting agents

To manufacture a 5% strength dusting agent, the following substances are used: 5 parts of 3,3',12,12'-tetramethyl-1,2-diazacyclododecatriene-1,5,9, 3 parts of precipitated silica and 92 parts of talc.

The active substance is intimately mixed with the carriers, and the mixture is ground.

Emulsion concentrate

To manufacture a 30% strength emulsion concentrate, 30 parts of 3,12-diethyl-1,2-diazacyclododeca-triene-1,5,9, 6 parts of octylphenol polyethylene glycol with 9-10 mols of ethylene oxide per mol of octylphenol, 6 parts of alkylarylsulphonate and 58 parts of xylene are mixed with one another. This concentrate can be diluted with water to give emulsions of suitable concentration.

Wettable powder

To manufacture a 25% strength wettable powder, the following constituents are used: 25 parts of 3,12-diisopropyl-1,2-diazacyclododecatriene-1,5,9, 20 parts of colloidal silica, 5 parts of sodium laurylsulphonate, 5 parts of naphthalenesulphonic acids-formaldehyde condensate and 45 parts of kaolin.

The active substance is absorbed on the carriers (silica and kaolin) and the whole is subsequently mixed and ground. A wettable powder of good wettability and ability to remain suspended is obtained. Suspensions of any desired active substance concentration can be obtained from this wettable powder by dilution with water.

What we claim is:

1. A 1,2-diaza-1,5,9-cyclododecatriene or 1,2-diaza-1-cyclododecene of the formula

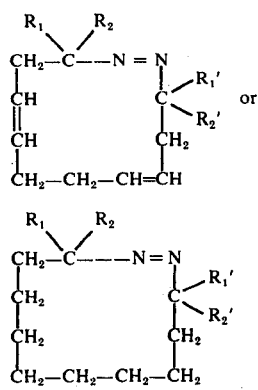

wherein
   $R_1$ and $R_1'$ independently of one another denote alkyl of one to six carbon atoms; alkenyl of up to four carbon atoms; alkyl of one to four carbon atoms substituted by phenyl; alkenyl of up to four carbon atoms substituted by phenyl; cyclohexyl; phenyl; phenyl substituted in the 4-position by a halogen atom, an alkyl of one to four carbon atoms or an alkoxy of one to four carbon atoms; 1-naphthyl; or 3,4-methylenedioxyphenyl;
   $R_2$ and $R_2'$ independently of one another denote hydrogen; alkyl of one to four carbon atoms; or
   $R_1$ and $R_2$, or $R_1'$ and $R_2'$, together with the carbon atoms to which they are bonded form a cycloalkyl ring of five to 12 carbon atoms.

2. A compound according to claim 1 wherein $R_1$ and $R_1'$ independently of one another denote alkyl of one to six carbon atoms; cyclohexyl; phenyl; 1-naphthyl; 4-methoxyphenyl; 3,4-methylenedioxyphenyl; 4-chlorophenyl; 4-methylphenyl; or styryl,
   $R_2$ and $R_2'$ independently of one another denote hydrogen or methyl, or
   $R_1$ and $R_2$, or $R_1'$ and $R_2'$, together with the carbon atoms to which they are bonded form a cycloalkyl ring of five to 12 carbon atoms.

3. A compound according to claim 1 wherein
   $R_1$ and $R_1'$ each represent alkyl of one to six carbon atoms; cyclohexyl; phenyl; 1-naphthyl; 4-methoxyphenyl; 3,4-methylenedioxyphenyl; 4-chlorophenyl; 4-methylphenyl; or styryl, and
   $R_2$ and $R_2'$ are hydrogen.

4. A compound according to claim 1 wherein
   $R_1$, $R_1'$, $R_2$ and $R_2'$ each represent alkyl of one to four carbon atoms.

5. A compound according to claim 1 wherein
   $R_1$ and $R_2$ as well as $R_1'$ and $R_2'$ each form, together with the carbon atom to which they are bonded, a cycloalkyl ring of five to 12 carbon atoms.

6. A compound according to claim 1, 3,12-diethyl-1,2-diaza-1,5,9-cyclododecatriene.

7. A compound according to claim 1, 3,12-diphenyl-1,2-diaza-1,5,9-cyclododecatriene.

8. A compound according to claim 1, 3,12-di(4-methoxyphenyl)-1,2-diaza-1,5,9-cyclododecatriene.

9. A compound according to claim 1, 3,3,12,12-tetramethyl-1,2-diaza-1,5,9-cyclododecatriene.

10. A compound according to claim 1, 3,12-diphenyl-1,2-diaza-1-cyclododecene.

11. A compound according to claim 1 having the formula

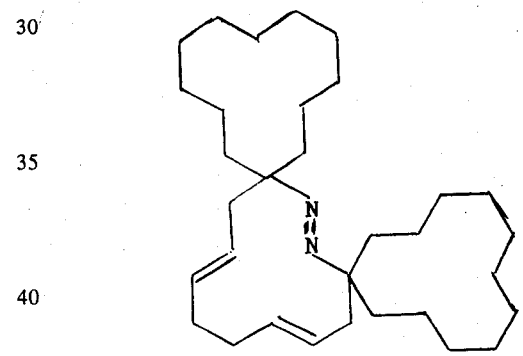

12. A process for the manufacture of the 1,2-diaza-1,5,9-cyclododecatrienes according to claim 1 which comprises
reacting 1,3-butadiene with an azine of the formula

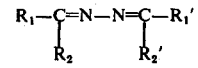

wherein $R_1$ and $R_1'$ independently of one another denote alkyl of one to six carbon atoms; alkenyl of up to four carbon atoms; alkyl of one to four carbon atoms substituted by phenyl; alkenyl of up to four carbon atoms substituted by phenyl; cyclohexyl; phenyl; phenyl substituted in the 4-position by a halogen atom, an alkyl of one to four carbon atoms or an alkoxy of one to four carbon atoms; 1-naphthyl; or 3,4-methylenedioxyphenyl; $R_2$ and $R_2'$ independently of one another denote hydrogen; alkyl of one to four carbon atoms; or $R_1$ and $R_2$, or $R_1'$ and $R_2'$, together with the carbon atoms to which they are bonded form a cycloalkyl ring of five to 12 carbon atoms; at a temperature below 100°C, under an inert atmosphere, in an anhydrous inert organic solvent, in the presence of previously isolated bis-cyclooctadiene-(1,5) nickel (0) complex catalyst or in the presence of a catalyst obtained by the reduction of a nickel compound, which is free of carbon monoxide, selected from the group consisting of nickel acetylacetonate, nickel dimethylglyoxime, nickel formate and dicyclopentadienyl nickel, with an organometallic compound free of halogen, in the presence of an electron donor Lewis base selected from the group consisting of cyclic ethers, alkylphosphines, arylphosphines, alkyl phosphites, aryl phosphites and the corresponding alkyl and aryl compounds of arsenic and antimony.

13. A process for the manufacture of the 1,2-diaza-1-cyclododecenes according to claim 1 which comprises reducing the corresponding 1,2-diaza-1,5,9-cyclododecatriene by catalytic hydrogenation.

14. A process according to claim 13 wherein said nickel compound is nickel acetylacetonate, said organometallic compound is ethoxy-diethyl-aluminum, and the Lewis base electron donor is triphenylphosphine.

15. The process according to claim 14 wherein the reaction is carried out at a temperature between 20° and 40°C.

* * * * *